(12) United States Patent
Vaglio et al.

(10) Patent No.: US 9,280,637 B2
(45) Date of Patent: Mar. 8, 2016

(54) MULTI-ACTION BUTTON FOR MOBILE DEVICES

(71) Applicant: CERNER INNOVATION, INC., Lenexa, KS (US)

(72) Inventors: Jay Christopher Vaglio, Kansas City, KS (US); Matt Ryan Anderson, Kansas City, MO (US)

(73) Assignee: CERNER INNOVATION, INC., Kansas City, KS (US)

( * ) Notice: Subject to any disclaimer, the term of this patent is extended or adjusted under 35 U.S.C. 154(b) by 58 days.

(21) Appl. No.: 13/711,177

(22) Filed: Dec. 11, 2012

(65) Prior Publication Data

US 2014/0097961 A1    Apr. 10, 2014

Related U.S. Application Data

(60) Provisional application No. 61/710,409, filed on Oct. 5, 2012.

(51) Int. Cl.
| | |
|---|---|
| *G08B 1/08* | (2006.01) |
| *G06F 19/00* | (2011.01) |
| *G08B 5/22* | (2006.01) |
| *H04W 4/16* | (2009.01) |
| *G06F 3/048* | (2013.01) |
| *G06Q 50/00* | (2012.01) |
| *H04M 3/00* | (2006.01) |
| *H04W 4/22* | (2009.01) |
| *H04M 1/725* | (2006.01) |

(52) U.S. Cl.
CPC .............. *G06F 19/322* (2013.01); *G06F 3/048* (2013.01); *G06F 19/3418* (2013.01); *G06Q 50/00* (2013.01); *G08B 5/22* (2013.01); *H04M 3/00* (2013.01); *H04W 4/16* (2013.01); *H04M 1/72519* (2013.01); *H04W 4/22* (2013.01)

(58) Field of Classification Search
CPC ...... G08B 25/016; G08B 25/14; A61G 12/00; A61B 5/0002; G06F 19/322; G06F 19/3418
USPC ............. 340/539.11, 573.1, 8.1, 669, 286.07, 340/502, 539.12, 691.6; 455/404.2, 404.1; 705/3, 2
See application file for complete search history.

(56) References Cited

U.S. PATENT DOCUMENTS

| | | | |
|---|---|---|---|
| 8,451,101 B2 * | 5/2013 | Somasundaram et al. | 340/286.07 |
| 2003/0163789 A1 * | 8/2003 | Blomquist | 715/526 |
| 2005/0151640 A1 * | 7/2005 | Hastings | 340/539.11 |
| 2007/0239488 A1 * | 10/2007 | DeRosso | 705/3 |
| 2008/0074951 A1 * | 3/2008 | Hubicki | 368/14 |
| 2010/0123587 A1 * | 5/2010 | Walls | 340/573.1 |
| 2010/0137693 A1 * | 6/2010 | Porras et al. | 600/301 |

(Continued)

OTHER PUBLICATIONS

Non-Final Office Action mailed Jan. 30, 2014 in U.S. Appl. No. 13/711,217, 8 pages.

(Continued)

*Primary Examiner* — Hoi Lau
(74) *Attorney, Agent, or Firm* — Shook, Hardy & Bacon L.L.P.

(57) ABSTRACT

Systems, methods, and computer-readable media for providing a multi-action button for mobile devices are provided. Alerts are received and multi-action buttons are determined corresponding to the alerts and clinicians associated with mobile devices. The multi-action buttons are displayed on the mobile devices.

20 Claims, 4 Drawing Sheets

(56) References Cited

U.S. PATENT DOCUMENTS

| | | | |
|---|---|---|---|
| 2010/0223071 A1* | 9/2010 | Kland et al. | 705/3 |
| 2011/0054946 A1* | 3/2011 | Coulter et al. | 705/3 |
| 2011/0196306 A1* | 8/2011 | De La Huerga | 604/151 |
| 2012/0075103 A1* | 3/2012 | Powell et al. | 340/573.1 |
| 2012/0169467 A1* | 7/2012 | Condra | 340/8.1 |
| 2012/0278104 A1* | 11/2012 | Traughber et al. | 705/3 |
| 2012/0284040 A1* | 11/2012 | Dupin | 705/2 |
| 2013/0009783 A1* | 1/2013 | Tran | 340/669 |
| 2013/0065569 A1* | 3/2013 | Leipzig et al. | 455/416 |
| 2013/0085798 A1 | 4/2013 | Spatola et al. | |
| 2013/0162424 A1* | 6/2013 | Treacy | 340/502 |
| 2013/0183923 A1* | 7/2013 | Brackett et al. | 455/404.2 |
| 2014/0051399 A1 | 2/2014 | Walker | |
| 2014/0070939 A1* | 3/2014 | Halverson et al. | 340/502 |
| 2014/0085080 A1* | 3/2014 | Carnes | 340/539.12 |

OTHER PUBLICATIONS

Final Office Action mailed Jun. 19, 2014 in related case, U.S. Appl. No. 13/711,217, 8 pages.

Final Office Action, mailed Jun. 19, 2014, in related case, U.S. Appl. No. 13/711,217, 8 pp.

Pre-Interview Communication, mailed Sep. 25, 2014, in related case, U.S. Appl. No. 13/711,206, 10 pp.

Notice of Allowance, mailed Sep. 29, 2014, in related case, U.S. Appl. No. 13/711,217, 27 pp.

First Action Interview Office Action dated Mar. 17, 2015 in U.S. Appl. No. 13/711,206, 8 pages.

* cited by examiner

MULTI-ACTION BUTTON FOR MOBILE DEVICES

CROSS REFERENCE TO RELATED APPLICATIONS

This application claims the benefit of U.S. Provisional Application No. 61/710,409, titled "MULTI-ACTION BUTTON FOR MOBILE DEVICES AND ATTACHING PATIENT CONTEXT TO A CALL HISTORY," filed Oct. 5, 2012, which is hereby expressly incorporated by reference in its entirety.

BACKGROUND

Patient medical information, such as that contained in the EMR, allows health care providers to provide continuity of care to patients. Thus, it is critical for clinicians providing care to patients to review and collaborate with other clinicians for each patient's medical record. However, these collaborations, while important to providing care for patients, often goes undocumented because the ability to track mobile voice communication as well as the content discussed is not currently available. This results in confusion and an inability to reference the details (e.g. patient name, relevant alerts, and the like) of a mobile voice call and leaves the clinician and healthcare entity unable to appropriately track such information that may otherwise be useful in analytics, tracking patient progress, billing, reimbursement, scheduling staff, and patient acuity.

Further, when receiving alerts regarding a particular patient, it is critical that these alerts are acknowledged in a timely manner. Often, it is necessary for an additional action to be taken in addition to acknowledging the alert. For example, the responding clinician may need to acknowledge (i.e., accept) the alert and call or text another clinician. Unfortunately, displays of current mobile devices are cluttered with option buttons which results in confusion and time lost pondering the correct action.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to providing a multi-action button for mobile devices. More particularly, an alert is received and a multi-action button is determined corresponding to the alert and a clinician associated with a mobile device and the multi-action button is displayed on the mobile device.

Accordingly, in one embodiment, computer storage media storing computer-executable instructions that, when executed by one or more computing devices, cause the one or more computing devices to perform a method that facilitates providing a multi-action button for mobile devices is provided. An alert is received at a mobile device associated with a clinician. A multi-action button is determined that corresponds to the alert and a role associated with the clinician. The multi-action button is displayed on the mobile device.

In another embodiment, a computer system to facilitate providing a multi-action button for mobile devices is provided. The computer system comprises a processor coupled to a computer storage medium, the computer storage medium having stored thereon a plurality of computer software components executable by the processor. An alert component receives an alert on a mobile device associated with a clinician. A multi-action button component determines a multi-action button that corresponds to the alert and a role associated with the clinician. A display component displays the multi-action button on the mobile device.

In another embodiment, computer storage media having computer-executable instructions embodied thereon that, when executed, produce a graphical user interface (GUI) to facilitate providing a multi-action button for mobile devices is provided. An alert display area that displays an alert on a mobile device associated with a clinician. A multi-action display area displays a multi-action button that corresponds to the alert and a role associated with the clinician.

BRIEF DESCRIPTION OF THE DRAWING

The present invention is described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention can positively impact health organizations' key imperatives in a variety of ways. Embodiments of the present invention provide multi-action buttons on mobile devices that can be utilized by clinicians to improve response time and availability.

Figure 1:
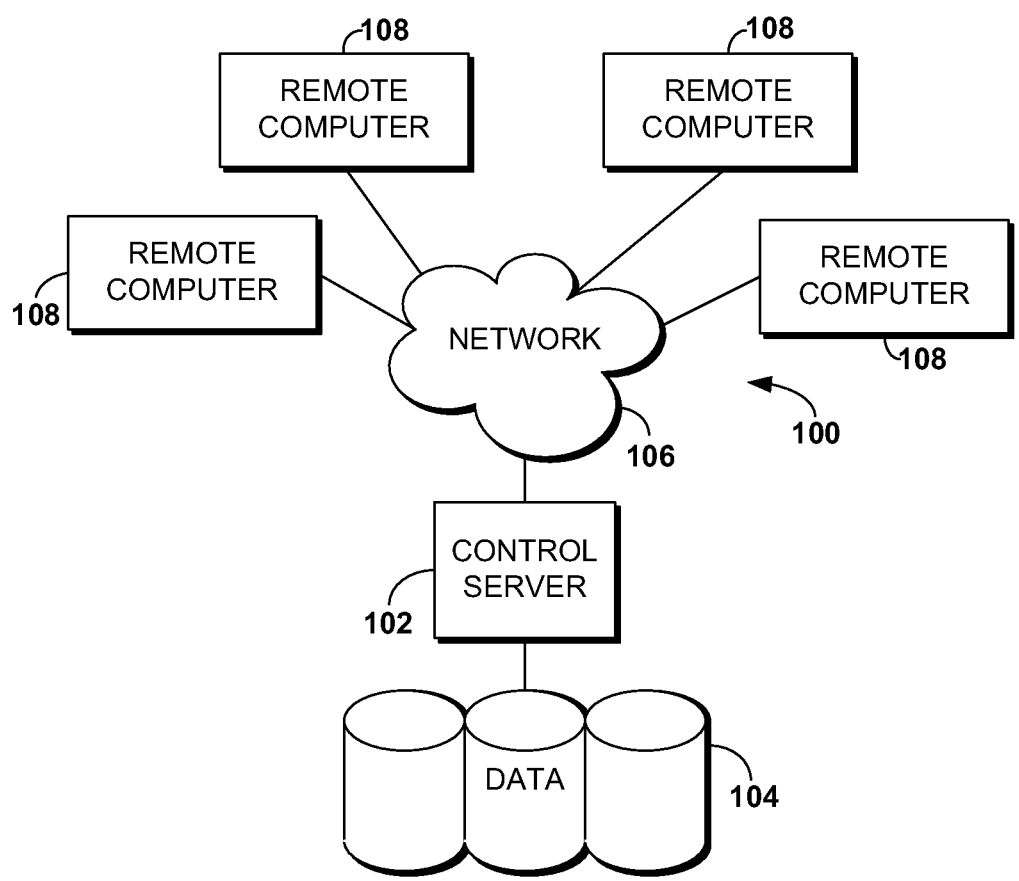
FIG. 1 is a block diagram of an exemplary computing environment suitable for use in implementing the present invention.

Referring now to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

Embodiments of the present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. Embodiments of the present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary computing system environment 100 includes a general purpose computing device in the form of a control server 102. Components of the control server 102 may include, without limitation, a processing unit, internal system memory, and a suitable system bus for coupling various system components, including database cluster 104, with the control server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes, or has access to, a variety of computer readable media, for instance, database cluster 104. Computer readable media can be any available media that may be accessed by server 102, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 102. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 104, provide storage of computer readable instructions, data structures, program modules, and other data for the control server 102. The control server 102 may operate in a computer network 106 using logical connections to one or more remote computers 108. Remote computers 108 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 108 may also be physically located in non-traditional medical care environments so that the entire health care community may be capable of integration on the network. The remote computers 108 may be personal computers, mobile devices, servers, routers, network PCs, peer devices, other common network nodes, or the like, and may include some or all of the components described above in relation to the control server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the control server 102 may include a modem or other means for establishing communications over the WAN, such as the Internet. In a networked environment, program modules or portions thereof may be stored in the control server 102, in the database cluster 104, or on any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., server 102 and remote computers 108) may be utilized.

In operation, a user may enter commands and information into the control server 102 or convey the commands and information to the control server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the control server 102. In addition to a monitor, the control server 102 and/or remote computers 108 may include other peripheral output devices, such as speakers and a printer.

Although many other internal components of the control server 102 and the remote computers 108 are not shown, those of ordinary skill in the art will appreciate that such components and their interconnections are well known. Accordingly, additional details concerning the internal construction of the control server 102 and the remote computers 108 are not further disclosed herein.

Figure 2:
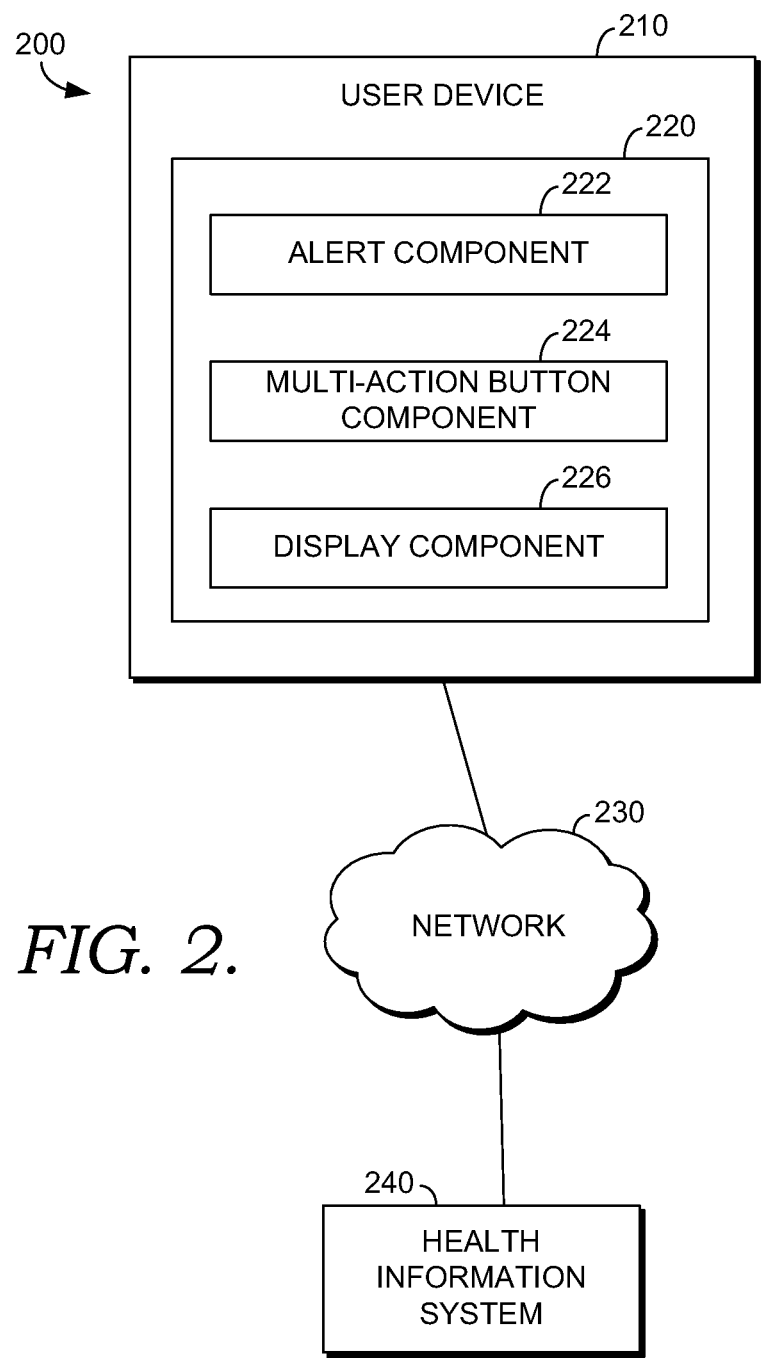
FIG. 2 is a block diagram of an exemplary system for providing a multi-action button for mobile devices, in accordance with embodiments of the present invention.

With reference to FIG. 2, a block diagram is illustrated that shows an exemplary computing system architecture for implementing embodiments of the present invention. It will be appreciated that the computing system architecture shown in FIG. 2 is merely an example of one suitable computing system and is not intended as having any dependency or requirement related to any single module/component or combination of modules/components.

The computing system 200 includes one or more user devices 210 (e.g., a mobile communication device), network 230, and health information system 240. User device 210 receives and displays data, such as alerts, from health information system 240 and communicates or otherwise makes the data available to multi-action engine 220. User device 210 also allows a clinician to respond to the alerts as well as communicate with other clinicians (e.g., text, voice communication, e-mail).

Multi-action engine 220 may reside on one or more computing devices, such as, for example, the control server 102 described above with reference to FIG. 1, user device 210, as shown in FIG. 2, or health information system 240. By way of example, the control server 102 includes a computer processor and may be a server, personal computer, desktop computer, laptop computer, handheld device, mobile device, consumer electronic device, or the like. Multi-action engine 220 comprises, in various embodiments, alert component 222, multi-action button component 224, and display component 224.

In one embodiment, alert component receives an alert on a mobile device associated with a clinician. For example, the alert may be an alert associated with a patient in healthcare facility. The alert may be sent to multiple clinicians associated with the healthcare facility. The alert may require acknowledgement or further action from one or more of the clinicians. The further action may be escalating the alert to another clinician. Escalating the alert may require a voice communication or text message to another clinician. Unfortunately, each of these actions, when made individually, waste valuable time. Interfaces displaying these actions individually appear cluttered and confusing to clinicians, wasting additional valuable time.

In one embodiment, multi-action button component 224 determines a multi-button that corresponds to the alert. For example, one alert may be more critical than another alert. The critical alert may require additional escalation or actions that can be integrated into a multi-action button that accomplishes the required escalations and actions. Display component 226 displays the multi-action button on the mobile device.

In one embodiment, the multi-action button further corresponds to a role associated with the clinician. For example, the role of a clinician may influence the escalation or actions that are integrated into a multi-action button. A medical assistant acknowledging an alert may, when acknowledging a particular alert, need to escalate the alert to the nursing staff, the attending physician, or even the critical response team. Another clinician may be required, upon acknowledging a particular alert, to take vitals that are entered into the medical device and populated into the EMR associated with that patient. In this example, acknowledging the alert may also automatically open a workflow directing the clinician to take the required vitals. In one embodiment, the multi-action button further corresponds to a proximity or location associated with the clinician. For example, the proximity or location of a clinician may make one clinician better situated to acknowledge and respond to an alert than another clinician. In this example, the clinician that is not well situated may have a multi-action button that, upon acknowledging the alert, escalates the alert to the clinician that is better situated to respond to the alert.

In one embodiment, the multi-action button further corresponds to a patient associated with the alert. The patient may have particular requirements or preferences in which clinicians an alert is escalated to. In this case, the clinician acknowledging the alert may have a multi-action button that includes escalating the alert to the required or preferred clinicians. For clarity, in any of the embodiments described herein, such a button may include segmented functionality such that when one portion of the button is selected, one action is taken, while another portion of the button is selected, another action is taken. Continuing the above example, portions of the button may acknowledge and escalate (i.e., call or text message) to other clinicians that may or may not be identified by a particular portion of the button. In one embodiment, the multi-action button further corresponds to a proximity or location associated with other clinicians.

In one embodiment, the multi-action button further corresponds to an availability associated with the clinician or other clinicians. For example, portions of the multi-action button may allow the responding clinician to acknowledge the alert and escalate to available clinicians. Portions of the multi-action button may identify available clinicians and may allow the responding clinician to simultaneously acknowledge the alert and call or text message the appropriate identified, available clinician.

Figure 3:
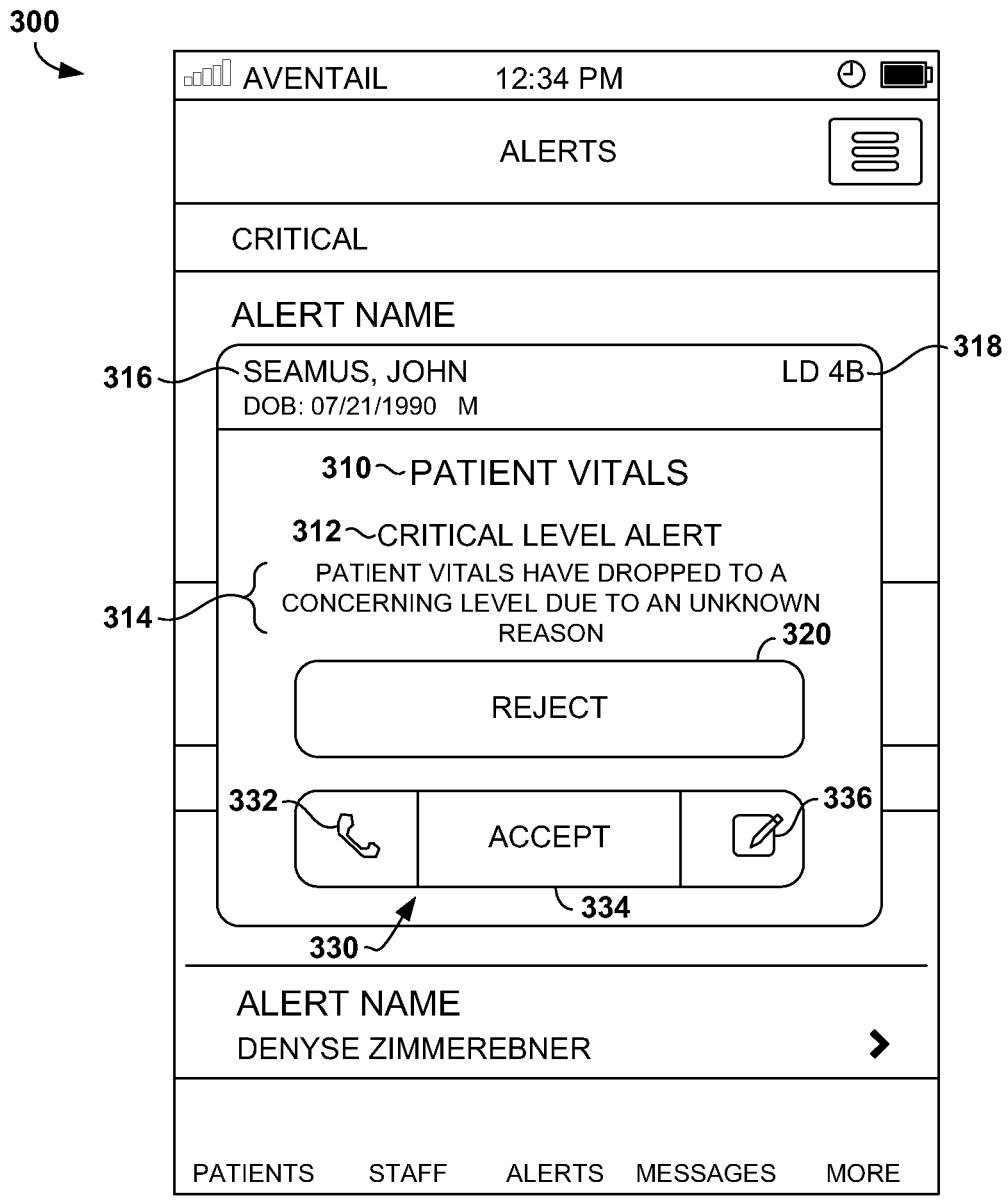
FIG. 3 is an illustrative graphical user interface display of a multi-action button, in accordance with an embodiment of the present invention.

Referring now to FIG. 3, an illustrative graphical user interface (GUI) 300 depicts a multi-action button, in accordance with embodiments of the present invention. GUI 300 includes alert display area 310 that displays on alert on the mobile device. The alert display area 310 includes, in one embodiment, an alert level 312. In another embodiment, alert display area 310 includes information 314 specific to the alert that may assist the clinician in determining whether to acknowledge and/or escalate the alert. In one embodiment, GUI 300 includes a reject button 320 for rejecting the alert. Rejecting the alert may cause the alert to be communicated or escalated to another clinician. In one embodiment, GUI 300 includes a patient information display area 316 that displays information associated with a patient corresponding to the alert. In one embodiment, patient display area 316 includes location information 318 that displays a location associated with the patient and/or alert. In one embodiment, GUI 300 includes a multi-action display area that displays a multi-action button 330 that corresponds to the alert and a role associated with the clinician.

The multi-action button 330 may be segmented such that different functions are provided by each segment. For example, segment 332 of multi-action button 330 accepts the alert and calls another clinician. In one embodiment, the second clinician that is called or who the alert is escalated to is identified by segment 332 so the determination of who to call or escalate the alert to is automatically made for the first clinician. Similarly, segment 336 of multi-action button 330 accepts the alert and opens a text messaging application for the first clinician to text message a second clinician regarding the alert. In one embodiment, a text message is automatically prepared and communicated to the second clinician based on the alert and/or role of the clinician. In another embodiment, the recipient of the text message is identified by segment 336 so the determination of who to text message or escalate the alert to is automatically made for the first clinician. In one embodiment, a third segment 334 of multi-action button 330 accepts the alert but takes no further action. Such acceptance may inform other clinicians that the first clinician is responding to the alert so the other clinicians do not lose time responding to an alert that is already accounted for. As can be appreciated, multi-action button 330 can be segmented into any number of segments streamlining the workflow for the clinician and building escalation intelligence into the display and function of the segments to ensure proper protocols are followed.

Figure 4:
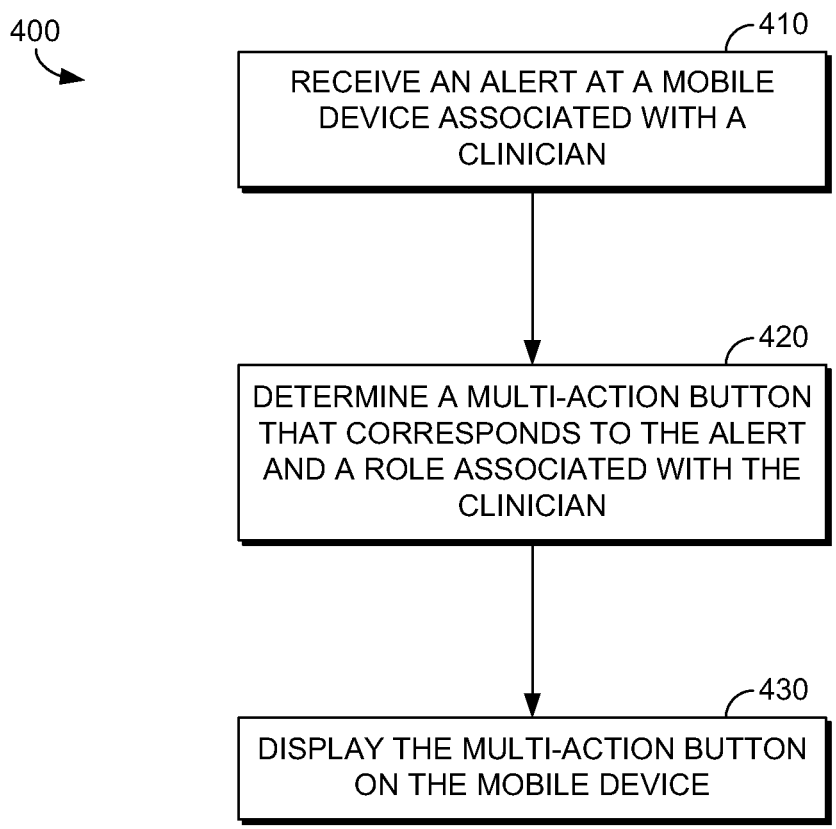
FIG. 4 is a flow diagram showing a method for providing a multi-action button for mobile devices, in accordance with an embodiment of the present invention.

Referring now to FIG. 4, an illustrative flow diagram 400 is shown of a method for providing a multi-action button for mobile devices, in accordance with embodiments of the present invention. At step 410, an alert is received at a mobile device associated with a clinician. A multi-action button is determined, at step 420 that corresponds to the alert. The multi-action button may further correspond to a role associated with the clinician. At step 430, the multi-action button is displayed on the mobile device.

Many different arrangements of the various components depicted, as well as components not shown, are possible without departing from the scope of the claims below. Embodiments of our technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

Having thus described the invention, what is claimed is:

1. One or more non-transitory computer storage media storing computer-executable instructions that, when executed by one or more computing devices, cause the one or more computing devices to perform a method that facilitates providing a multi-action button for mobile devices:
    receiving an alert at a mobile device associated with a clinician;
    determining a multi-action button that corresponds to the alert and a role associated with the clinician; and
    displaying the multi-action button on the mobile device, wherein the multi-action button includes segmented functionality such that when one portion of the button is selected, the alert is accepted and another clinician is called, while another portion of the button is selected, a text messaging application is opened for the clinician to text message a second clinician regarding the alert, wherein the text message is automatically prepared and communicated to the second clinician based on the alert and/or role of the clinician.

2. The media of claim 1, wherein the alert is associated with a patient in a healthcare facility.

3. The media of claim 1, further comprising requiring acknowledgment or further action from the clinician that are integrated into the multi-action button.

4. The media of claim 1, wherein the multi-action button corresponds to a role associated with the clinician.

5. The media of claim 3, wherein acknowledging the alert automatically opens a workflow directing the clinician to perform an action.

6. The media of claim 1, wherein the multi-action button corresponds to a proximity or location associated with the clinician.

7. The media of claim 1, wherein the multi-action button corresponds to a patient associated with the alert.

8. The media of claim 1, wherein portions of the multi-action button identify other clinicians to escalate the alert.

9. The media of claim 1, wherein the multi-action button corresponds to a proximity or location associated with other clinicians.

10. The media of claim 1, wherein the multi-action button corresponds to an availability associated with other clinicians.

11. The media of claim 1, further comprising escalating the alert to another clinician.

12. The media of claim 11, wherein escalating the alert to another clinician requires the clinician to include a voice communication or text message.

13. The media of claim 1, wherein portions of the multi-action button allow the clinician to simultaneously acknowledge the alert and call or text message an identified, available clinician.

14. A computer system to facilitate providing a multi-action button for mobile devices, the computer system comprising a processor coupled to a non-transitory computer storage medium, the non-transitory computer storage medium having stored thereon a plurality of computer software components executable by the processor, the computer software components comprising:
    an alert component for receiving an alert on a mobile device associated with a clinician;
    a multi-action button component for determining a multi-action button that corresponds to the alert and a role associated with the clinician; and
    a display component for displaying the multi-action button on the mobile device, wherein the multi-action button includes segmented functionality such that when one portion of the button is selected, the alert is accepted and another clinician is called, while another portion of the button is selected, a text messaging application is opened for the clinician to text message a second clinician regarding the alert, wherein the text message is automatically prepared and communicated to the second clinician based on the alert and/or role of the clinician.

15. The system of claim 14, wherein the multi-action button component determines the multi-action button that further corresponds to a proximity or location associated with other clinicians.

16. The system of claim 14, wherein the multi-action button component determines the multi-action button that further corresponds to an availability associated with other clinicians.

17. Non-transitory computer storage media having computer-executable instructions embodied thereon that, when executed, produce a graphical user interface (GUI) to facilitate providing a multi-action button for mobile devices, the GUI comprising:
    an alert display area that displays an alert on a mobile device associated with a clinician; and
    a multi-action display area that displays a multi-action button that corresponds to the alert and a role associated with the clinician, wherein the multi-action button includes segmented functionality such that when one portion of the button is selected, the alert is accepted and another clinician is called, while another portion of the button is selected, a text messaging application is opened for the clinician to text message a second clinician regarding the alert, wherein the text message is automatically prepared and communicated to the second clinician based on the alert and/or role of the clinician.

18. The media of claim 17, wherein the GUI further comprises a patient display area that displays information associated with a patient corresponding to the alert.

19. The media of claim 17, wherein the multi-action button is segmented with each segment performing a different function.

20. The media of claim 17, wherein the GUI further comprises a reject display area that displays a reject button for rejecting the alert and causing the alert to be communicated or escalated to another clinician.

\* \* \* \* \*